US010212938B1

(12) United States Patent
     Culpepper

(10) Patent No.: US 10,212,938 B1
(45) Date of Patent: *Feb. 26, 2019

(54) PANEL ASSEMBLY WITH INTERSTITIAL COPPER

(71) Applicant: Modular Services Company, Oklahoma City, OK (US)

(72) Inventor: Taylor C. Culpepper, Oklahoma City, OK (US)

(73) Assignee: Modular Services Comopany, Oklahoma City, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/807,097

(22) Filed: Jul. 23, 2015

Related U.S. Application Data

(63) Continuation of application No. 13/853,675, filed on Mar. 29, 2013, now Pat. No. 9,113,634.

(60) Provisional application No. 61/618,819, filed on Apr. 1, 2012.

(51) Int. Cl.
    *A01N 25/34* (2006.01)
    *A01N 59/20* (2006.01)

(52) U.S. Cl.
    CPC ............. *A01N 59/20* (2013.01); *Y10T 428/16* (2015.01)

(58) Field of Classification Search
    CPC .............................. Y10T 428/16; A01N 25/34
    USPC ....................................................... 428/44, 58
    See application file for complete search history.

(56) References Cited

U.S. PATENT DOCUMENTS

| 3,389,041 | A  | * | 6/1968  | Hundhausen | B44C 5/04 144/346 |
| 4,755,410 | A  | * | 7/1988  | Cohen      | B44C 5/08 428/192 |
| 2004/0062899 | A1 | * | 4/2004  | Kobayashi  | A47G 27/025 428/48 |
| 2012/0251756 | A1 | * | 10/2012 | Buckley    | C09J 7/0296 428/41.8 |
| 2013/0047537 | A1 | * | 2/2013  | Dao        | E04F 15/18 52/309.3 |
| 2013/0117936 | A1 | * | 5/2013  | Stryker    | A61G 7/05 5/600 |

* cited by examiner

*Primary Examiner* — Alexander S Thomas
(74) *Attorney, Agent, or Firm* — Mary M. Lee

(57) ABSTRACT

The present invention provides a panel assembly comprising a plurality of panels arranged in edge-to-edge format having joints between each pair of adjacent panels in the assembly. A copper-containing material, such as copper tape with adhesive backing, is provided in or near the joints in the assembly to render the joints less susceptible to bacterial contamination.

10 Claims, 3 Drawing Sheets

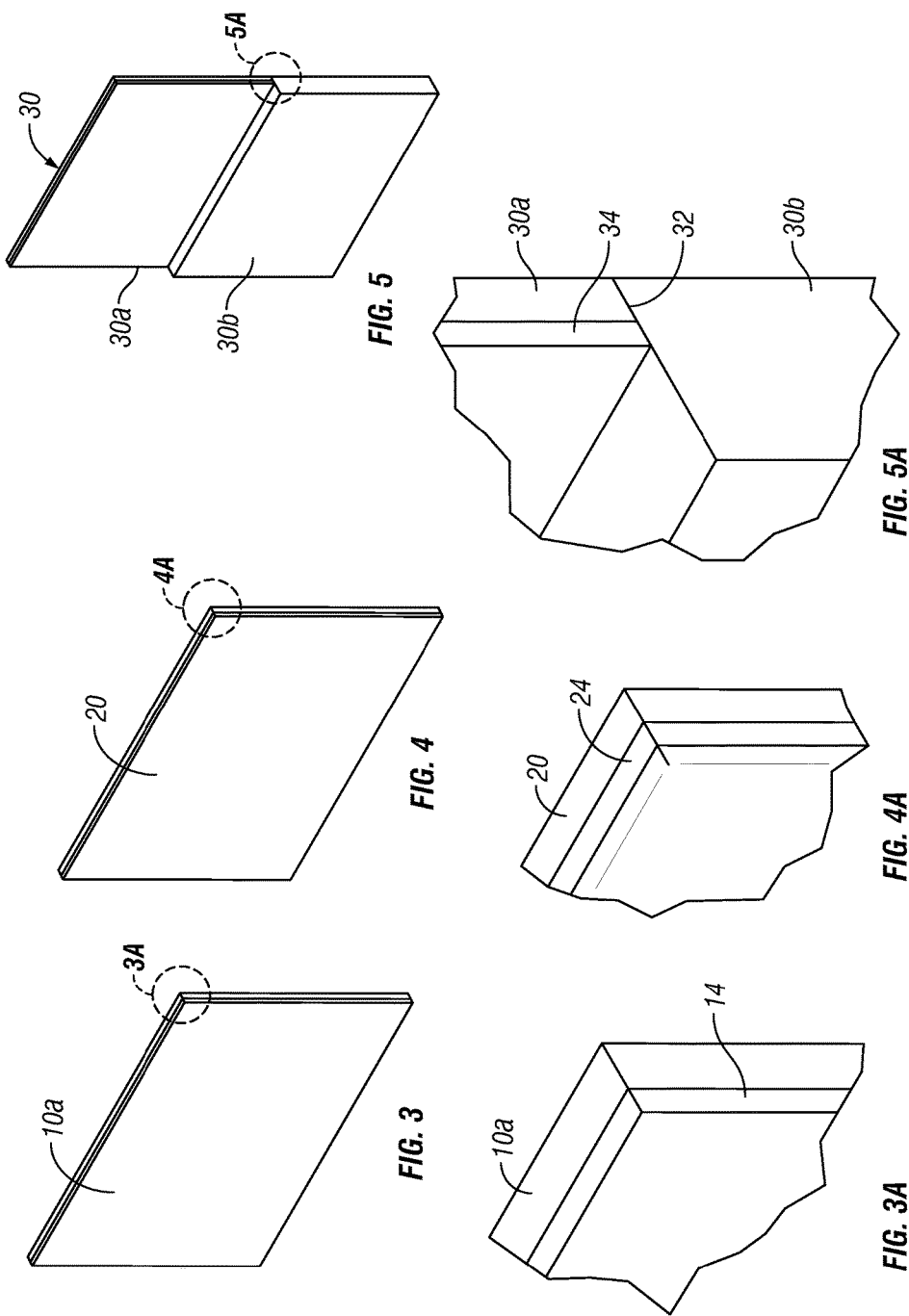

PANEL ASSEMBLY WITH INTERSTITIAL COPPER

CROSS-REFERENCE TO RELATED APPLICATIONS

This application is a continuation of application Ser. No. 13/853,675, entitled "Panel Assembly with Interstitial Copper," filed Mar. 29, 2013, now U.S. Pat. No. 9,113,634, issued Aug. 25, 2015, which claims the benefit of the filing date of U.S. provisional application No. 61/618,819 entitled "Copper Augmented Panel," filed Apr. 1, 2012, and the contents of these applications are incorporated herein by reference.

FIELD OF THE INVENTION

The present invention relates generally to panel assemblies and more particularly to panel assemblies comprising interstices and the treatment such panel assemblies to render the interstices antibacterial.

BRIEF DESCRIPTION OF THE DRAWINGS

The accompanying drawings, which are incorporated into and form a part of the specification, illustrate one or more embodiments of the present invention and, together with this description, serve to explain the principles of the invention. The drawing merely illustrates a preferred embodiment of the invention and is not to be construed as limiting the scope of the invention.

FIG. 2b is an enlarged view of the segment identified as "C" in FIG. 2a.

FIG. 3 is a perspective view of a panel segment with a square edge.

FIG. 3a is an enlarged perspective view of the segment identified as "D" in FIG. 3.

FIG. 4 is a perspective view of a panel segment with a radiused edge.

FIG. 4a is an enlarged perspective view of the segment identified as "E" in FIG. 4.

FIG. 5 is a perspective view of a panel assembly with a complex joint.

FIG. 5a is an enlarged perspective view of the segment identified as "F" in FIG. 5.

DETAILED DESCRIPTION OF THE PREFERRED EMBODIMENT(S)

Current research and practices dating back hundreds of years show that copper possesses highly efficient antibacterial properties that kill nearly all types of bacteria, all within a couple of hours of contact. The healthcare industry is increasing its efforts to control the growing infection contamination issues by many methods, and antibacterial surfaces are one of those tools. Many surfaces may be decontaminated with solutions. However, many surfaces contain or create joints and crevices that cannot be effectively accessed for decontamination. Any copper alloy that contains at least about 65% copper that can be applied to these locations can deactivate most all bacteria in a matter of hours thus supplementing other methods of infection control.

Figure 1A:
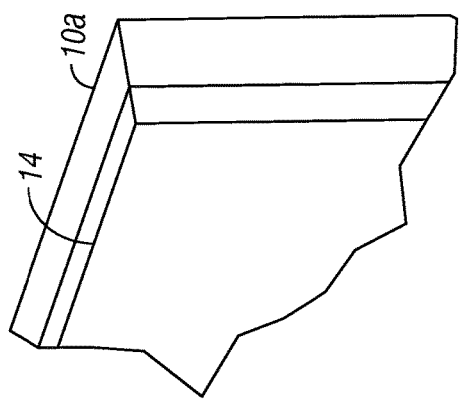
FIG. 1a is an enlarged view of the segment identified as "A" in FIG. 1.
Figure 1:
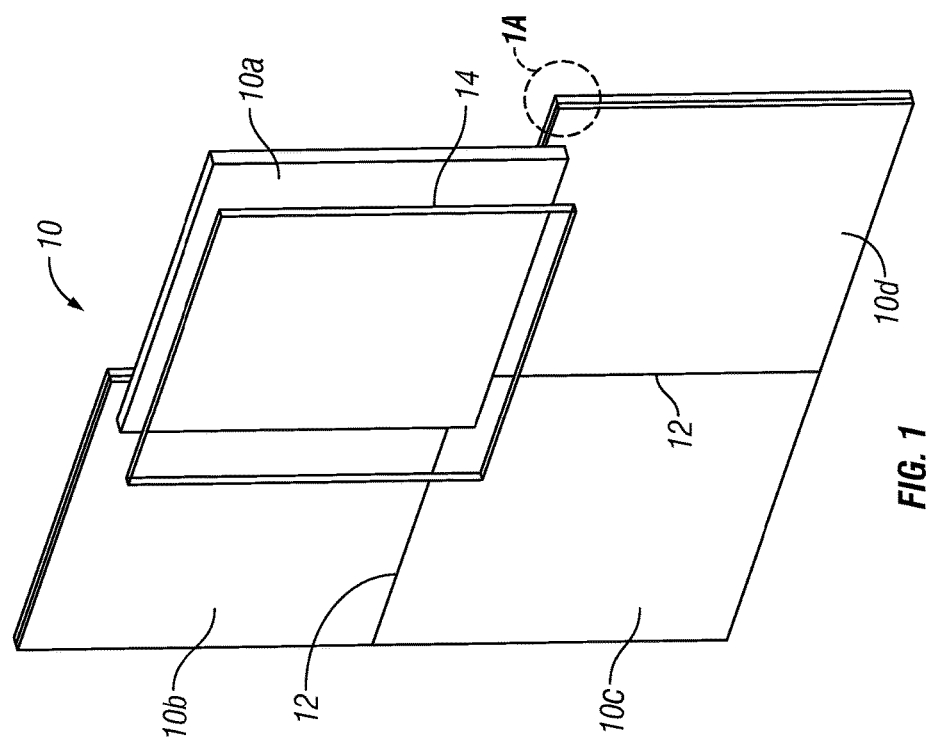
FIG. 1 is a partly exploded, perspective view of a panel assembly constructed in accordance with a preferred embodiment of the present invention.

Turning now to the drawings in general and to FIG. 1 in particular there is therein a panel assembly constructed in accordance with a first preferred embodiment of the present invention and designated generally by the reference number 10. The illustrative panel assembly 10 comprises four panels 10a, 10b, 10c, and 10d arranged in a two-by-two pattern. This panel assembly 10 may be provided as a decorative element on a wall or the surface of furniture. It may form part of the exposed surface of various architectural structures in hospitals and other industrial or commercial establishments where the growth of bacterial or other harmful microbes is a problem. The term "panel" as used herein is to be construed broadly to mean any structure comprising a broad continuous surface circumscribed by an edge. It may be planar or contoured.

Although the panels are arranged close together in an edge to edge format, there is present between the edges of adjacent panels a small joint or interstitial space designated generally at 12. As shown in FIG. 1, the broad flat outer surfaces "S" of this panel assembly 10 may be treated easily and effectively with various solutions. However, because it is difficult for liquids to penetrate the small interstitial joints, these spaces may harbor bacteria.

In accordance with the present invention, the panel assembly 10 is provided with an edging of copper alloy or copper impregnated material to render the interstitial spaces that are exposed to the outer surface of the panel assembly resistant to bacterial growth. When the complete perimeter of each of the panels in a group of panels contains a copper containing element, bacteria contacting the copper are deactivated in a matter of hours thereby preventing the colonization of bacteria. Moreover, the copper exhibits a "halo" effect that disinfects the region immediately surrounding the copper containing element.

Figure 2A:
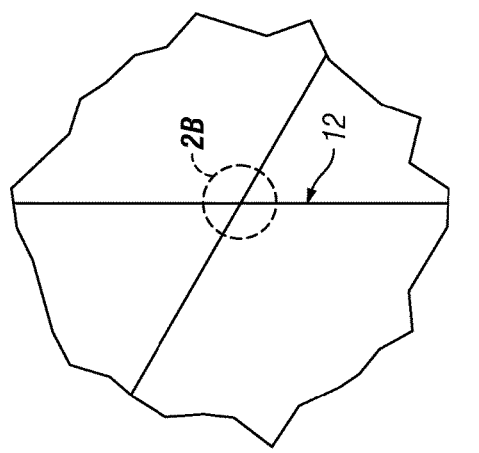
Figure 2B:
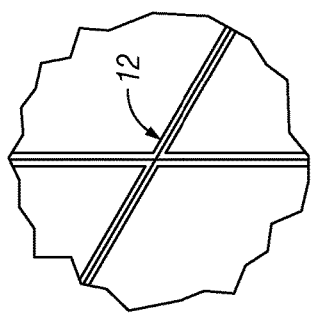
Figure 2:
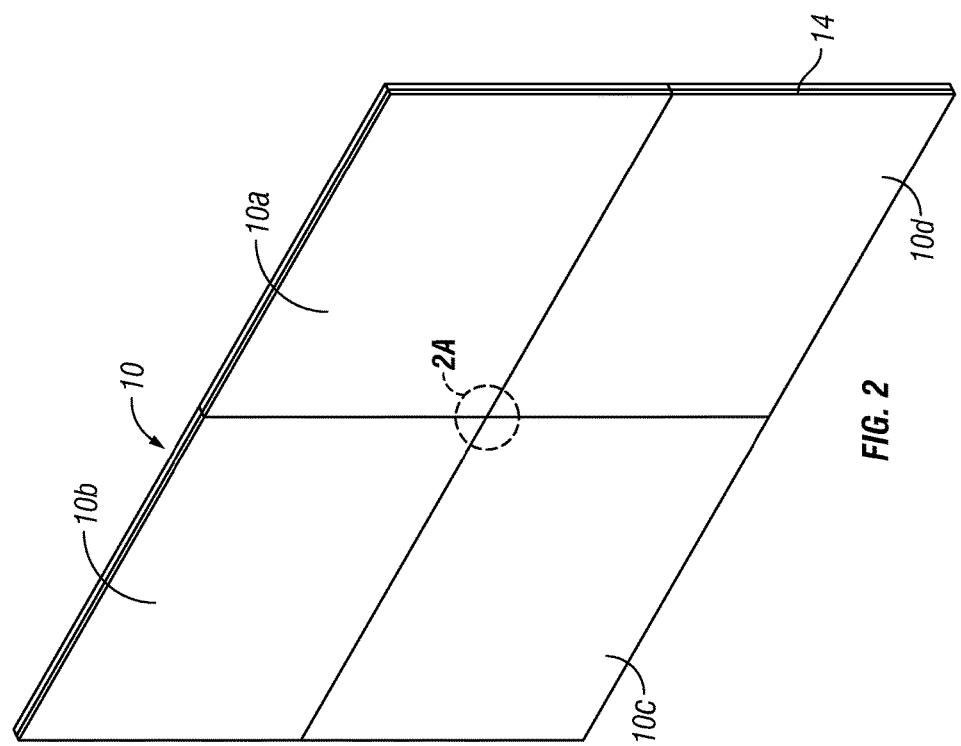
FIG. 2 is a non-exploded perspective view of the panel assembly of FIG. 1.

To that end, in accordance with the embodiment illustrated in FIG. 1, each of the panels 10a, 10b, 10c, and 10d is provided with a strip 14 of adhesive-backed, copper-containing tape around its edge. One suitable type of tape is electromagnetic shielding tape, although other ways of providing this edging may be employed. The preferred edging comprises an effective amount of copper, that is, an amount of copper sufficient to reduce the population of bacteria in the interstitial space either by direct contact or by the "halo" effect. More preferably, the antibacterial material comprises an amount of copper effective to kill at least about ninety percent (90%) of bacteria in the interstitial space. Still more preferably, the antibacterial material comprises an amount of copper effective to kill at least about ninety-nine percent (99%) of bacteria in the interstitial space. In most instances, the copper-containing material will comprise at least about sixty-five percent (65%) by weight copper. As best seen in FIG. 1a, the copper strip 14 is applied to the front perimeter of each panel 10a, 10b, 10c, and 10d. The position of the copper element 14 in the assembled panels 10 is best seen in FIGS. 2, 2a, and 2b.

As indicated previously, there are several modes of applying or depositing an antibacterial copper containing composition to the panel assembly of the present invention. The shape and position of the copper strip previously described may vary depending on the particular configuration of the panels and more specifically the profile of the panel's edge. Examples are shown in FIGS. 3, 3a, 4, 4a, 5, and 5a.

In the embodiment of FIGS. 3 and 3a, the panel 10a has a square configuration as in FIGS. 1 and 1a. In FIGS. 4 and 4a, the profile of the edge of the panel 20 is radiused. On the radiused edge, the strip 24 is applied to the side below or behind where the curve begins; this will prevent buckling or wrinkling of the tape.

FIGS. 5 and 5a show a panel assembly 30 comprising two panels 30a and 30b, with the panel 30b having a greater thickness providing a joint 32 with a complex profile. In this embodiment, the copper edging 34 is applied only to the edge of the upper panel 30a. This ensures that at least one strip of copper containing material is present in the interstitial space 32 between the adjacent edges of the panels.

In all of the embodiments of the present invention illustrated in the drawings, the copper containing material is a strip of tape. However, it will be understood that the copper containing material may take other forms, such as a liquid that is brushed, sprayed or painted on the surface, or a thicker composition that extruded into the joints of an assembled group of panels. Thus, the copper containing material may be positioned or deposited using several different techniques depending on the nature of the composition. Still further, while the location of the applied copper edging shown in the accompanying drawings is on the side surfaces of the panels, near the front, other locations may work equally well. For example, the antibacterial material may be formed in or applied to the surface on which the panels are supported rather directly on the panel edges. Further still, while in the preferred embodiments, each panel is edged with copper prior to the joinder of the panels into a complete panel assembly, it may be equally advantageous to apply the antibacterial material after the panels are assembled.

Regardless of the form of the copper material or the technique by which it is applied to the panel edges, the copper-containing material is selected and applied to the edges or sides of said panels or in the interstices of such panels or structures in such a way that, when assembled, there is provided in the interstices an effective amount of copper, that is, an amount of copper sufficient to render bacteria unable to survive or propagate beyond the copper element and its associated "halo" effect. In embodiments where a joint is formed between a panel and trim or other non-butt type joint, the copper strip or tape can be applied between members to again eliminate crevices were bacteria could avoid cleaning and disinfectants. Examples are shown in the accompanying drawings. However, the copper may be positioned, extruded, or deposited in any manner either on the edges of the panels, assembled or unassembled, or in the grooves or crevices in the assembled panels, or between the panel and supporting surfaces.

The embodiments shown and described above are exemplary. Many details are often found in the art and, therefore, many such details are neither shown nor described herein. It is not claimed that all of the details, parts, elements, or steps described and shown were invented herein. Even though numerous characteristics and advantages of the present inventions have been described in the drawings and accompanying text, the description is illustrative only. Changes may be made in the details, especially in matters of shape, size, and arrangement of the parts within the principles of the inventions to the full extent indicated by the broad meaning of the terms of the attached claims. The description and drawings of the specific embodiments herein do not point out what an infringement of this patent would be, but rather provide an example of how to use and make the invention. Likewise, the abstract is neither intended to define the invention, which is measured by the claims, nor is it intended to be limiting as to the scope of the invention in any way. Rather, the limits of the invention and the bounds of the patent protection are measured by and defined in the following claims.

What is claimed is:

1. A panel assembly having an outer surface, the panel assembly adapted for installation on a structure in a space so that the outer surface of the panel assembly is exposed to human contact, wherein the structure comprises an outer surface at least partially circumscribed by an edge, and wherein the panel assembly comprises:
   at least one panel, wherein each of the at least one panel comprises an outer surface circumscribed by a peripheral edge, and wherein when the panel assembly is configured so that, when the panel assembly is installed, at least a portion of the peripheral edge of the at least one panel and at least a portion of the edge of the structure are arranged in edge-to-edge formation forming an interstitial space therebetween that at least partly defines an open crevice in the outer surface of the panel assembly when the panel assembly is installed;
   a deposit of antibacterial material disposable around the peripheral edge of the at least one panel, and wherein the antibacterial material comprises an amount of copper sufficient to render the open crevice bactericidal when the panel assembly is installed; and
   wherein the at least one panel and the deposit of antibacterial material are configured so that, when the panel assembly is installed and the deposit of antibacterial material is disposed around the peripheral edge of the at least one panel, the outer surface of the structure and the outer surface of the panel assembly beyond the open crevice are free of the antibacterial material.

2. The panel assembly of claim 1 wherein the antibacterial material comprises an adhesive tape.

3. The panel assembly of claim 2 wherein the adhesive tape is positioned on the edge of at least one of the plurality of panels.

4. The panel assembly of claim 2 wherein the adhesive tape is positioned on the edge of each one of the plurality of panels.

5. The panel assembly of claim 1 wherein the antibacterial material comprises at least about sixty-five percent copper by weight.

6. The panel assembly of claim 1 wherein the antibacterial material is further defined as capable of killing at least about ninety percent (90%) of bacterial within about two hours.

7. The panel assembly of claim 6 wherein the antibacterial material is further defined as capable of killing at least about ninety-nine percent (99%) of bacterial within about two hours.

8. The panel assembly of claim 1 wherein the antibacterial material is positioned on the edge of at least one of the plurality of panels.

9. The panel assembly of claim 1 wherein the structure in the space is an architectural structure.

10. The panel assembly of claim 1 wherein the structure in the space is an architectural structure.

* * * * *

UNITED STATES PATENT AND TRADEMARK OFFICE
CERTIFICATE OF CORRECTION

PATENT NO. : 10,212,938 B1
APPLICATION NO. : 14/807097
DATED : February 26, 2019
INVENTOR(S) : Taylor C. Culpepper Page 1 of 1

It is certified that error appears in the above-identified patent and that said Letters Patent is hereby corrected as shown below:

In the Specification
Column 1, Line 12: replace "Apr. 1, 2012," with --Apr. 1, 2012, now expired--.
Column 1, Line 39: Insert the following sentence before paragraph starting with "FIG 2b". --FIG. 2a is an enlarged view of the segment identified as "B" in FIG. 2.--.
Column 3, Line 42: replace "were" with --where--.
Column 3, Line 55: replace "inventions" with --invention--.
Column 3, Line 59: replace "inventions" with --invention--.

In the Claims
Column 4, Line 50: replace "bacterial" with --bacteria--.
Column 4, Line 53: replace "bacterial" with --bacteria--.

Signed and Sealed this
Sixteenth Day of April, 2019

Andrei Iancu
*Director of the United States Patent and Trademark Office*